United States Patent [19]
Li

[11] Patent Number: 6,132,462
[45] Date of Patent: Oct. 17, 2000

[54] COPOLYMERS FORMED FROM THREE COMPONENTS AND INTRAOCULAR LENSES MADE THEREOF

[75] Inventor: Fumian Li, Beijing, China

[73] Assignees: Santen Pharmaceutical Co., Ltd., Osaka, Japan; Fumian LI, Beijing, China

[21] Appl. No.: 09/102,397

[22] Filed: Jun. 22, 1998

Related U.S. Application Data

[63] Continuation-in-part of application No. PCT/CN96/00115, Dec. 23, 1996.

[30] Foreign Application Priority Data

Dec. 22, 1995 [CN] China .................... 95 1 20427

[51] Int. Cl.$^7$ .................................................. A61F 2/16
[52] U.S. Cl. ............................. 623/6.11; 351/160 M; 524/91; 524/359; 524/558; 526/258; 526/320; 526/328.5
[58] Field of Search .................. 524/91, 359, 558; 526/258, 320, 328.5; 623/6.11; 351/160 H

[56] References Cited

U.S. PATENT DOCUMENTS

| | | | |
|---|---|---|---|
| 4,123,407 | 10/1978 | Gordon | 523/108 |
| 4,240,163 | 12/1980 | Galin | 623/6 |
| 4,304,895 | 12/1981 | Loshaek | 526/313 |
| 4,343,927 | 8/1982 | Chang | 526/262 |
| 4,528,311 | 7/1985 | Beard et al. | 524/91 |
| 4,582,865 | 4/1986 | Balazs et al. | 524/29 |
| 4,834,750 | 5/1989 | Gupta | 623/6 |
| 4,956,432 | 9/1990 | Vacik et al. | 526/264 |
| 5,147,394 | 9/1992 | Siepser et al. | 63/6 |
| 5,217,491 | 6/1993 | Vanderbilt | 623/6 |
| 5,290,548 | 3/1994 | Goldberg et al. | 424/78.18 |
| 5,290,892 | 3/1994 | Namdaran et al. | 526/259 |
| 5,331,073 | 7/1994 | Weinschenk, III et al. | 526/264 |
| 5,359,021 | 10/1994 | Weinschenk, III et al. | 526/264 |
| 5,716,403 | 2/1998 | Tran et al. | 623/6 |

FOREIGN PATENT DOCUMENTS

| | | |
|---|---|---|
| 234 749 | 9/1987 | European Pat. Off. . |
| 330 164 | 8/1989 | European Pat. Off. . |
| 53-105250 | 9/1978 | Japan . |
| 2-8218 | 1/1990 | Japan . |
| 2-43208 | 2/1990 | Japan . |
| 4-28705 | 1/1992 | Japan . |
| 5-80279 | 4/1993 | Japan . |
| 5-150197 | 6/1993 | Japan . |
| 2 223 230 | 4/1990 | United Kingdom . |

OTHER PUBLICATIONS

Polymer Handbook, 2nd Edition, Edited by J. Brandrup et al., John Wiley & Sons, 1975.

Primary Examiner—Robert Dawson
Assistant Examiner—Kuo-Liang Peng
Attorney, Agent, or Firm—Frishauf, Holtz, Goodman, Langer & Chick, P.C.

[57] ABSTRACT

A foldable intraocular lens material which includes 60 to 80 weight % of $$-(CH_2-\underset{\underset{\underset{\underset{OH}{|}}{R^2}}{\overset{\overset{\overset{R^1}{|}}{|}}{C}}}{|})-,$$

wherein $R^1$ is hydrogen or alkyl, and $R^2$ is unsubstituted alkylene or alkylene substituted by a hydroxyl group; 10 to 30 weight % of $$-(CH_2-\underset{\underset{R^3}{|}}{\overset{\overset{R^1}{|}}{C}})-,$$

(with pyrrolidone N-substituent)

wherein $R^3$ is a single bond or $$-O-(CH_2)_m-,\quad -HN-(CH_2)_n-\text{ or}$$
$$-(CH_2)_p-O-(CH_2)_q-,$$

wherein $R^5$, $R^6$, $R^7$ and $R^8$ are hydrogen or alkyl, m, n, p and q are integers from 1 to 4, and $R^4$ is hydrogen or alkyl; and 5 to 20 weight % of $$-(CH_2-\underset{\underset{\underset{R^{10}}{|}}{O}}{\overset{\overset{R^9}{|}}{C}})-,$$

wherein $R^9$ is hydrogen or alkyl and $R^{10}$ is alkyl.

34 Claims, No Drawings

COPOLYMERS FORMED FROM THREE COMPONENTS AND INTRAOCULAR LENSES MADE THEREOF

This application is a continuation-in-part application of International Application PCT/CN96/00115 filed Dec. 23, 1996.

FIELD OF THE INVENTION

The invention relates to copolymers useful for ocular lens, especially preferable for foldable intraocular lens (foldable IOL).

BACKGROUND OF THE INVENTION

Crystalline lens could be replaced by intraocular lens (IOL) in cataract surgery. Since IOL was first used in transplanting in 1949, various research effects have been carried out on IOL materials. As there is a great evolution on operation methods, with the advancement of operation methods, demands on the characteristics of IOL have also changed a lot. Recently, with the popularity of the phacoemulsification procedure, it is possible to open a very small incision to extract opaque crystalline lens and finish the operation. So demands on characteristics of implanted IOL have changed continuously. For example, characteristics of so-called foldable IOL make it possible to implant through the small incision in foldable form and open in the lens capsule. At the same time, various research effects have been carried out on IOL materials. Usually, polymethyl methacrylate (PMMA), silicone, acrylic and resin are widely used as the IOL materials, while polysiloxane and acrylic resin can be used as foldable IOL materials. Copolymers of ethoxyl methacrylate and methyl methacrylate may also have been used recently. On the other hand, during the studies on these kinds of material, in order to prevent from the effect of UV ray on the retina, they can contain an UV absorber such as hydoxylbenzophenone, hydroxylphenyl benzotriazole and so on. Moreover, in order to raise biocompatibility and prevent from deposition of cells, a polysaccharide such as heparin is coated on the IOL surface in practice.

There have been reports on the polymers whose partial structure unit is acrylic acid monomer with a characteristic pyrrolidone group in the present invention, especially those used in ocular lens, such as a copolymer of methacryloyloxyethyl-2-pyrrolidone and acrylic acid (JP Laid-Open 28705/1992), a polymer polymerized from the monomer which is formed from amidation of acrylic acid and pyrrolidone (JP Laid-Open 43208/1990), a polymer of polyoxyalkylene structure with a pyrrolidone group (JP Laid- Open 8218/1990) and so on. As for copolymers formed from three components, there have been reports only on a copolymer of vinyl pyrrolidone, ethoxyl methacrylate and methyl methacrylate (JP Laid-Open 105250/1978), a copolymer of the methacryloyloxy ethyl-2-pyrrolidone, alkyl methacrylate and fluoroalkyl methacrylate (JP Laid-Open 150197/1993). Moreover, the main object of these studies is the application on soft contact lens and not on IOL. There have been no report especially on the possibility of application of foldable IOL in the invention.

PROBLEMS TO BE SOLVED BY THE INVENTION

The object of the present invention is the application of an ocular lens, in detail, the application of a foldable IOL. During the studies on foldable IOL material, it is necessary to consider refractive index, tensile strength and recovery speed of the material. For example:

1) If the refractive index is too low, the thickness of IOL increases too much; if refractive index is too high, contraction difference of periphery becomes large. So it is necessary to choose a proper refractive index. In the concrete, the preferable range is 1.4–1.6.
2) Because tweezers are used to implant foldable IOL, tensile strength bearing their operation is needed.
3) After foldable IOL are implanted, they must be recovered to their original form in the lens capsule. Recovering speeds vary with the difference of the custom and competence among operators. The possibility of mechanical bruise of peripheral tissue usually increases with the acceleration of recovering speed. On the other hand, with the slowdown of recovering speed and the elongation of the operation, the possibility of mechanical bruise of peripheral tissue increases. Therefore, for the foldable IOL, a suitable recovering speed is needed.

Moreover, the characteristics of being shaped easily should be taken into consideration.

Based on these opinions, various foldable IOL can be used in practice, while it is hopeful to develop more preferable material.

THE RESOLUTION OF THE PROBLEMS

The inventor, with the consideration of the above problems, studied on the results of more applicable material of foldable IOL and found that a copolymer of a hydroxyl alkyl acrylate derivative, an alkyl acrylate derivative and an acrylic acid derivative with a pyrrolidone group could be used especially as good material.

SUMMARY OF THE INVENTION

The present invention relates to the copolymers polymerized from the monomers represented by the following (a), (b) and (c), and the copolymers comprises the following structure units [I], [II] and [III], the process for preparing copolymers and ocular lens formed from the copolymers.

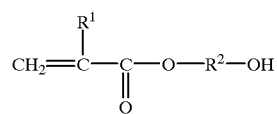

a)

Wherein $R^1$ represents a hydrogen atom or a lower alkyl group, and $R^2$ represents a lower alkylene which can be substituted by a hydroxyl group, moreover, there may be an oxygen atom in the alkylene chain.

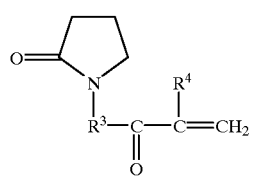

b)

Wherein $R^3$ represents

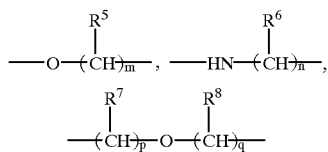

or a single bond, in which $R^5$, $R^6$, $R^7$ and $R^8$ respectively represent a hydrogen atom or a lower alkyl group and m, n, p and q are integers from 1 to 4, and $R^4$ represents a hydrogen atom or a lower alkyl group.

c)

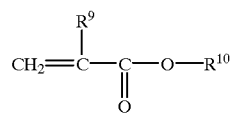

Wherein $R^9$ represents a hydrogen atom or a lower alkyl group, $R^{10}$ represents lower alkyl group.

When structure units are used to represent the copolymer, the copolymer is composed of the following structure units [I], [II], and [III], wherein it comprises 60–80 wt % of [I], 10–30 wt % of [II] and 5–20 wt % of [III], based on the total weight of 100 wt %.

[I]

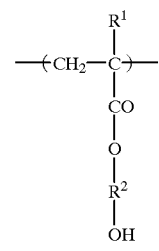

[II]

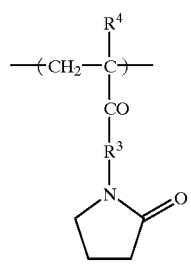

[III]

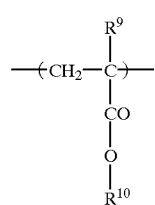

In the above formulas, said lower alkyl group is straight or branched chain alkyl groups having 1 to 6 carbon atoms such as methyl, ethyl, propyl, isopropyl, buthyl, isobutyl, hexyl; lower alkylene group is straight or branched chain alkylene groups having 1 to 6 carbon atoms such as $-CH_2-$, $-(CH_2)_2-$, $-(CH_2)_3-$, $-CH(CH_3)_2-$, $-(CH_2)_4-$, $-(CH_2)_6-$. In the above description, especially, the preferable example is that $R^1$ represents a hydrogen atom or a methyl group, $R^2$ represents $-(CH_2)_2-$ or $-(CH_2)_3-$, $R^3$ represents $-OCH_2-$, $-OCH_2CH_2-$, $-NHCH_2-$ or a single bond, $R^4$ represents a hydrogen atom or a methyl group, $R^9$ represents a hydrogen atom or methyl a group and $R^{10}$ represents a methyl group or an isobutyl group.

It is preferable to combine the above groups. Especially, the preferable combination is that $R^1$ represents a methyl group, $R^2$ represents $-(CH_2)_2-$, $R^3$ represents $-OCH_2CH_2-$, $R^4$ represents a methyl group, $R^9$ represents a methyl group and $R^{10}$ represents a methyl group.

Concerning the structure unit ratios of the copolymer in the present invention, preferably, the content of [I] is 65–75 wt %, the content of [II] is 15–25 wt % and the content of [III] is 5–15 wt %, based on the total weight of 100 wt %, more preferably, the content of [I] is 70 wt %, the content of [II] is 21 wt % and the content of [III] is 9 wt %.

According to the present invention, it is preferable that $R^1$ represents a hydrogen atom or a methyl group, $R^2$ represents $-(CH_2)_2-$ or $-(CH_2)_3-$, $R^3$ represents $-OCH_2-$, $-OCH_2CH_2-$, $-NHCH_2-$ or a single bond, $R^4$ represents a hydrogen atom or a methyl group, $R^9$ represents a hydrogen atom or a methyl group, $R^{10}$ represents a methyl or an isobutyl group, the content of [I] is 60–80 wt %, the content of [II] 10–30 wt % and the content of [III] 5–20 wt %, based on the total weight of 100 wt %. More preferably, $R^1$ represents a methyl group, $R^2$ represents an ethylene group, $R^3$ represents $-OCH_2CH_2-$, $R^4$ represents a methyl group, $R^9$ represents a methyl group, $R^{10}$ represents a methyl group, the content of [I] is 70 wt %, the content of [II] is 21 wt % and the content of [III] is 9 wt %.

Monomers a), b) and c), using potassium persulfate, ammonium persulfate, benzophenone or methacryloyloxy hydroxylbenzophenone as a polymerization initiating agent, could be copolymerized to well synthesize the copolymers of the present invention.

Generally, azodiisobutyronitrile is most widely used as a polymerization initiating agent in copolymer the synthesis, but when it is used in synthesis of foldable IOL material which is the application purpose of the present invention, the mechanical strength of the material is not satisfactory. The inventor precisely studied on polymerization initiating agents and found that when potassium persulfate, ammonium persulfate, benzophenone or methacryloyloxy hydroxylbenzophenone is used as a polymerization initiating agent, foldable material with satisfactory mechanical strength could be obtained.

On the other hand, the molecular weight of the copolymer of the present invention (viscosity-average molecular weight) only needs to be ten thousand or over. Generally, the molecular weight has no great effect on the characteristics of the copolymers, and it is not an important factor, but it has effect on the strength of the copolymers. The relation between the molecular weight and the strength of the copolymers is about a linear proportional relation when the molecular weight is lower than ten thousand, but if the molecular weight is higher than ten thousand, the strength of the copolymers attains a maximum value and the value accesses a constant value. Therefore, when the molecular weight is lower than ten thousand; strength the of the copolymers are not stable and it is likely to be troublesome when the copolymers used as foldable IOL, but when the molecular weight is higher than ten thousand, there is no problem. However, if the molecular weight is too high, the strength of the copolymers used as foldable IOL is not preferable. So the preferable range of the molecular weight of the copolymers is from ten thousand to one hundred thousand. The molecular weight of the copolymers in the following examples is also within the range.

In accordance with the composition of the present invention, through selecting properly the ratio of every component, refractive index, tensile strength, recovering speed can be designed according to needs. For example, when the ratio of structure unit [I] increases, there is almost no effect on refractive index and recovering speed, but there is a slight decreasing trend in tensile strength; when the ratio of structure unit [II] increases, refractive index increases, there is almost no effect on recovering speed, but there is a little decreasing trend in tensile strength. When the ratio of structure unit [III] increases, recovering speed and tensile strength increase, but there is a little decreasing trend in refractive index. Through good use of these characteristics, it is possible to obtain the expected foldable IOL. The preferable ratio of each structure unit is the same as the above description. If the preferable component ratio is used, refractive index is 1.4–1.6, recovering speed is not too fast or too slow, i.e. 3–6 seconds, and tensile strength is just the one which could fully bear tweezers operation, that is to say, after implantation in eyes (being swollen-wetted), foldable IOL with tensile strength being 10 psi or over could be obtained. On another occasion, according to the custom of the operator, recovering speed could be designed to be 3–6 seconds with 2 seconds variation amplitude.

There are hydrophilic and hydrophobic foldable IOL, and they are used respectively according to purpose. The copolymers of the present invention are hydrophilic. Hydrophilic foldable IOL would be stored under a dry condition.

Before utilization, being swollen and wetted with distilled water, foldable IOL are implanted in eyes. It is possible to reckon hydrophilic extents in accordance with the rate of water content. But, hydrophilic extents have an effect on biological affinity and softness of foldable IOL. Under the circumstances of the present invention, it is possible to choose the rate of water content by selecting the ratio of every structure unit. For example, if the ratios of structure units [I] and [II] increase, the rates of water content increase; if the ratio of structure unit [III] increases, the rate of water content decreases. For the rate of water content, the preferable range is 25–50%.

UV absorbers are widely used in IOL in order to prevent a bad effect on the retina, and the copolymers of the present invention can also contain a UV absorber to some extent. There are two methods to contain an UV absorber: Containing an UV absorber with a physical method and combining an UV absorber with the copolymers with chemical method. In the present invention, the two methods could also be used. Especially with the chemical method, there is an advantage that the UV absorber would not be left out from IOL when IOL are used.

The chemical combination is that the UV absorber itself which has polymerizable double bond, may be copolymerized with the above monomers to form the copolymers. The content of the UV absorber is very little to the total weight, and it has almost no effect on the characteristics of the copolymers. But if the content of the UV absorber is too much, the copolymers become brittle. The preferable range of content of the UV absorber is 0.5–2.0 wt %, and the more preferable range is 0.8–1.5 wt %.

There is no special limits on the varieties of UV absorbers, so long as they are used in IOL. For example, benzophenone, benzotriazole series or their acrylic acid derivatives, in the concrete, hydroxylbenzophenone, hydroxylbenzotriazole or their acrylic acid derivatives such as 4-methacryloyloxy-2-hydroxylbenzophenone are used as UV absorbers.

The copolymers of the present invention can be cross linked between molecules. Physical strength and rate of water content can be adjusted through cross-linking. Compounds of the acrylate or acrylamide series can be used as the cross-linking agent, for example, ethylene glycol bismethacrylate, diethylene glycol bismethacrylate or N,N'-methylene bisacrylamide. When the content of the cross-linking agent is too much, the copolymers would become hard and recovering speed would become fast, however, the copolymers become brittle. The preferable the range of content of cross- linking agent is 0.01–2.0 wt %, the more preferable range is 0.1–1.5 wt % and the most preferable range is 0.5–1.0 wt %.

In order to raise biocompatibility and prevent from deposition of cells, the technique of polysaccharide coating on the IOL surface has been used recently. Because there are free hydroxyl groups on the terminals of the copolymers of the present invention, which can combine with a polysaccharide by a covalent bond, separation of the coatings doesn't occur. Moreover, it is possible to make a covalent bond form easily. For example, divinyl sulfone could do the job. Preferably, the polysaccharide is heparin, hyaluronic acid or its salt such as sodium salt, potassium salt and so on.

Moreover, as a characteristic of the copolymers of the present invention, the value of monomer reactivity ratio $r_1 \times r_2$ (MRR) of acrylic acid derivatives with a pyrrolidone group, that is to say, components b) and a), accesses 1.0. The value of $r_1 \times r_2$ accessing 1.0 means ideal polymerization. If component a) is 2-hydroxyethyl methacrylate and component b) is N-pyrrolidonoethyl acrylate, the value of $r_1 \times r_2$ is 1.03. The testing method of MRR is in accordance with the Mayo-Lewis Method (J. Am. Chem. Soc., 1994, 66, 1594).

The present invention relates to IOL material a having flexible and soft property. After an operation with tweezers, marks of tweezers remain and it must take some time to recover to its original form. But the problem could be resolved because the copolymers of the present invention have good recovering ability.

After implantation of usual silicone series IOL, if a laser is used to cure secondary cataract, crystalline lens often become opaque and transparency would be damaged. On another occasion, there may be slight denaturation on the periphery, then the visual field would be damaged to some extent. However, when the copolymers of the present invention are used, an opaque lens would not be found, transparency would be maintained and there would be no denaturation on the periphery. The copolymers of the present invention could form easily applied foldable IOL. The shaping method has been reported in public. The copolymers of the present invention are especially preferable for foldable IOL, and they are also preferable to be used on soft contact lens.

The present invention is further explained by the following examples of its practice.

REFERENCE EXAMPLE (SYNTHESIS OF MONOMER)

Reference Example 1

Synthesis of 2-(2-pyrrolidone-1-yl) ethyl acrylate(PyEA)
Into the solution of 1-(2-hydroxyethyl)-2-pyrrolidone (50 ml) and triethylamine (85 ml) dissolved in chloroform (150 ml), the solution of acryloyl chloride (50 ml) dissolved in chloroform (100 ml) was dropped in two hours with stirring. The reactive solution was stirred at 4° C. for 20 hours, then at 50° C. for 2 hours, after cooling, the solution was filtered. The filtrate was washed with 15% of sodium carbonate aqueous solution, then concentrated under vacuum. The obtained oily material was distillated under vacuum. The yield of the title compound is 70%.

bp: 112–13° C./0.5 Torr

NMR (ppm, TMS, CDCl$_3$): 6.14 (m, 3H), 5.80 (s, 1H), 4.30 (t, 2H), 3.60 (m, 4H), 2.20 (m, 4H)

IR (KBr, cm$^{-1}$): 1735, 1676, 1639, 1361

With the similar synthesis method to described in Example 1, the following compounds were synthesized.

2-(2-pyrrolidone-1-yl) ethyl methacrylate (PyEMA)

bp: 120–122° C./0.5 Torr

NMR (ppm, TMS, CDCl$_3$): 6.10 (s, 3H), 5.59 (s, 1H), 4.29 (t, 2H), 3.59 (m, 4H), 2.30 (m, 4H), 1.94 (m, 3H)

IR (KBr, cm$^-$): 1735, 1676, 1639, 1361

2-pyrrolidone-1-ylmethyl acrylate (PyMA)

bp: 92–93° C./0.5 Torr

NMR (ppm, TMS, CDCl$_3$): 6.34–6.83 (m, 2H), 6.06–6.12 (m, 1H), 5.37 (m, 2H), 3.57–3.69 (m, 2H), 1.91–2.50 (m, 4H)

IR (KBr, cm$^-$): 1708, 1639, 1415

2-pyrrolidone-1-ylmethyl methacrylate (PyMMA)

bp: 95–96° C./0.5 Torr

NMR (ppm. TMS, CDCl$_3$): 6.13–6.16 (s, 1H), 5.59–5.61 (m, 1H), 5.41 (s, 2H), 3.55 (t, 2H), 1.9–2.43 (m, 4H), 1.96 (m, 3H)

IR (KBr, cm$^-$): 1716, 1636, 1420

Reference Example 2

Synthesis of N-(2-pyrrolidone-1-ylmethyl)acrylamide (PyMAm)

The mixture of 1-methoxy methyl-2-pyrrolidone (65.6 g), acrylamide (75.5 g), toluene sulfonic acid (0.20 g) and phenothiazine (0.20 g) was stirred under the condition of N$_2$ for 1 hour at 150° C. while removing methanol by distillation. The residue was cooled, then recrystallized in acetone to give the title compound in the yield of 40%.

mp: 73–74° C.

NMR (ppm, TMS, CDCl$_3$): 7.31 (m, 1H), 6.19–6.31 (m, 2H), 5.56–5.72 (m, 1H), 4.75–4.81 (d, 2H), 3.50–3.66 (t, 2H), 1.91–2.44 (m, 4H)

IR (KBr, cm$^{-1}$): 3440, 1680, 1200–1600

With the similar synthesis method to described in Example 2, the following compounds were synthesized.

N-(2-pyrrolidone-1-ylmethyl) methacrylamide (PyMMAm)

mp: 101–102° C.

NMR (ppm, TMS, CDCl$_3$): 6.70 (s, 1H), 5.69 (s, 1H), 5.35 (s, 1H), 4.70–4.80 (d, 2H), 3.45–3.62 (t, 2H), 1.95–2.45 (m, 7H)

Reference Example 3

Synthesis of 1-acryloyl-2-pyrrolidone (NAPy)

2-pyrrolidone and acryloyl chloride were used to synthesize the title compound with the similar synthesis method to described in Example 1.

The yield of title compound was 70%.

bp: 85–86° C./0.5 Torr

NMR (ppm. TMS, CDCl$_3$): 7.31–7.65 (m, 1H), 6.56–6.59 (m, 1H), 5.74–5.96 (m, 1H), 3.77–3.96 (m, 2H), 2.52–2.73 (m, 2H), 1.85–2.24 (2m, 2H)

IR (KBr, cm$^-$): 1737, 1679, 1408

With the similar synthesis method to described in Example 3, the following compounds were synthesized.

1-methacroyl-2-pyrrolidone (NMAPy)

bp: 88–89° C./0.5 Torr

NMR (ppm. TMS, CDCl$_3$): 5.28–5.34 (s, 2H), 3.72–3.90 (m, 2H), 2.57–2.67 (m, 2H), 2.00–2.16 (m, 2H), 1.97–1.99 (s, 3H)

IR (KBr, cm$^-$): 1745, 1676, 1403

EXAMPLES

Synthesis of copolymers and preparation of the sheet formed from the copolymers

Example 1

Synthesis of copolymer (HEMA-PyEMA-MMA) of 2-hydroxyethyl methacrylate (HEMA), 2-(2-pyrrolidone-1-yl)ethyl methacrylate (PyEMA) and metyl methacrylate (MMA), and preparation of the sheet formed from the copolymer Into the mixture of HEMA, PyEMA and MMA with mixing volume ratio 70:20:10 (weight ratio 70:21:9), 0.2 wt % of potassium persulfate and 10 wt % of water were added, then the mixture was added to the 0.5 mm or 0.1 mm inter space of separators and the spacer between two glass plates fixed with holder. The size of the glass plates is 6 cm×5 cm, and they were treated with sealing agent of siloxane series and were fixed by attachment clip. The mixture was free radical-polymerized at 60° C. for 22 hours, then at 90° C. for 2 hours, then the mixture was treated and the polymerization was finished. After those, the sheet was taken off from the glass plates, dipped into distilled water to remove unreacted monomers, then the copolymer sheet as purpose was obtained. Moreover, size of the spacer between the two glass plates could be chosen according to needs.

With the similar preparation to described in Example 1, the following copolymers and their sheets were obtained.

HEMA-PyEA-MMA, HEMA-PyMA-MMA, HEMA-PyMMA-MMA, HEMA-NAPy-MMA, HEMA-PyMAm-MMA, HEMA-PyMMAm-MMA, HEA-PyEA-MA, HEA-PyMAm-MA, HPMA-PyEA-MMA, HEMA-PyE.

The above abbreviations represent the following compounds.

HEMA: 2-hydroxylethyl methacrylate
HEA: 2-hydroxylethyl acrylate
HPMA: 2-hydroxylpropyl methacrylate
NAPy: 1-acryloyloxy-2-pyrrolidone
PyEA: 2-(2-pyrrolidone-1-yl) ethyl acrylate
PyEMA: 2-(2-pyrrolidone-1-yl) ethyl methacrylate
Py MA: 2-pyrrolidone-1-yl methyl acrylate
PyMMA: 2-pyrrolidone-1-ylmethyl methacrylate
PyMAm: N-(2-pyrrolidone-1-ylmethyl) acrylamide
PyMMAm: N-(2-pyrrolidone-1-yl-methyl) methacrylamide
MMA: methyl methacrylate
MA: methyl acrylate
i-BuMA: isobutyl methacrylate
NMAPy: 1-methacryloyl-2-pyrrolidone The copolymers and their sheets could be prepared with the similar method to described in the following Example 2.

Example 2

Synthesis of copolymers with photopolymerizaiton and preparation of their sheets Into the mixture of HEMA, PyEMA and MMA with mixing volume ratio 70:20:10 (weight ratio 70:21:9), 2 wt % of benzophenone or 4-methacryloyloxy-2-hydroxylbenzophenone and 0.4 wt % of N, N'-dimethylaminoethyl methacrylate were added, then the mixture was added into the 0.5 mm or 0.1 mm inter space of separators and the spacer between two glass plates fixed with holder. The size of the glass plates is 6 cm×5 cm. They were treated with sealing agent of siloxane series and were fixed by attachment clip. The mixture was exposed under UV light of 80 w mercury lamp for 48 hours to be photopolymerized. Then the sheet was taken off from the glass plates, dipped into distilled water to remove unreacted monomers, then the copolymer sheet as purpose was obtained. Moreover, the size of the spacer between the two glass plates, could be chosen according to needs.

Example 3

Synthesis of the Cross Linked Copolymers and Preparation of Their Sheet

In Example 1, into the mixture before radical polymerization, 1.0 wt % of ethyleneglycol bismethacrylate (EGMA) was added. The following procedures were similar as that of Example 1, then the cross linked copolymer and its sheet were obtained.

In stead of EGMA, bismethacrylate such as diethyleneglycol bismethacrylate (DEGMA), bisacrylamide such as N, N'-methylene bisacrylamide can be used. On another occasion, content of cross-linking agent could be chosen according to needs.

Physiochemical properties of the copolymers sheets in Examples 1 or are shown in table 1. In the table, the copolymers marked with asterisk (*) were synthesized with methods of Example 3. Others were synthesized with methods of Example 1 and Example 2, the synthetic method is photopolymerization, but physiochemical properties of the obtained copolymer are same as those of the copolymer of Example 1.

TABLE 1

| Copolymer | Rate of water content | Refractive index | Tensile strength wet | Tensile strength dry | Recovering speed |
|---|---|---|---|---|---|
| HEMA-PyEA-MMA | 34 | 1.45 | 29.2 | 1,000 | Qualified |
| HEMA-PyEMA-MMA | 31 | 1.45 | 32.1 | 1,050 | Qualified |
| HEMA-PyMA-MMA | 33 | 1.45 | 82.3 | 2,313 | Qualified |
| HEMA-PyMMA-MMA | 28 | 1.44 | 193.6 | 806 | Qualified |
| HEMA-NAPy-MMA | 33 | 1.46 | 58.1 | 2,389 | Qualified |
| HEMA-PyMAm-MMA* | 40 | 1.44 | 41.4 | — | Qualified |
| HEMA-PyMMAm-MMA* | 36 | 1.45 | 65.9 | — | Qualified |
| HPMA-PyEA-MMA* | 40 | 1.43 | 19.2 | — | Qualified |
| HEMA-PyEA-i-BuMA* | 31 | 1.45 | 51.3 | — | Qualified |

*Cross-linked copolymers synthesized with method of Example 3.

Physiochemical properties in Table 1 were tested with the following methods.

Rate of water content: Copolymer sheet cut in disc form was added into water at 0° C. for more than 2 days. After water content was in equilibrium, water on the surface was wiped out and weighed the sheet weight, that is $W_1$. Then the copolymer sheet was dehydrated under vacuum at 60° C. for 48 hours. The weight of the dry copolymer was $W_2$.

Rate of water content is calculated with $(W_1-W_2)/W_1$.

Refractive index: Tested with Abbe refractive machine.

Tensile strength: Tested at 12cm/min tensile speed with YQ-Z-7 equipment. Unit is represented with psi. The so-called "wet" represents equilibrium state when the sheet being swollen and wetted by water and "dry" represents the state when the sheet was prepared.

Recovering speed: Sheet in equilibrium state when being swollen and wetted by water was cut in the size 3.0×3.0 cm. After it was folded by tweezers, time of recovering to original state was tested. The applicable time is about 3–6 seconds with 2 seconds variation amplitude and as long as the time is in the range of 3–6 seconds, it is called "qualified."

Example 4

Synthesis of the Copolymer with UV Absorber and Its Sheet

In Example 1, into the mixture before radical polymerization, 0.8–1.5 wt % of 4-methacryloxy-2-hydroxylbenzophenone (MAHBP) was added and followed by the similar procedure to Example 1, the copolymer combined with UV absorber in the form of chemical bond and its sheet were obtained.

When UV spectrum of the sheet was tested with Shimazu UV-250 machine, it was found that the sheet had good absorption under 400 nm. Absorption range could change through selecting UV absorber.

Example 5

Treating of Sheet Surface with Polysaccharide

The copolymer sheet prepared in Example 1 was added into 5% of heparin aqueous solution and stored for 24 hours, then exposed in air for 1 hour. After those, the sheet was dipped into sodium carbonate buffer solution (pH 11) with 0.1% of diethyl sulfone at 40° C., then the sheet was washed with phosphoric acid buffer solution, and washed fully with water. In the sheet, heparin was combined with hydroxyl group in state of covalent bond.

Sodium hyaluronate could be used as polysaccharide to replace heparin, and the similar sheet could be obtained.

Reference Example 4

Testing of Monomer Reactivity Ratio (MRR)

Testing monomer reactivity ratio (MRR) of acrylic acid derivative with pyrrolidone group which has the characteristic of monomer component of the copolymers in the present invention, such as PyEA, and the corresponding polymerizable monomer such as HEMA.

PyEA whose content varied in the range of 1 to 10 parts was mixed with one part HEMA, then azodiisobutyronitrile was added as polymerization initiating agent, and the mixture was placed into a sealed glass container with a gas outlet. The mixture was treated at 60° C. for 10–45 minutes to control the content of polymer below 10%. After reaction, the copolymer was precipitated in petroleum ether. Based on the analysis of nitrogen content, content of PyEA in the copolymer was determined. In accordance with Mayo-Lewis Method (J. Am. Chem. Soc., 1994, 66, 1594), reactive ratio $r_1$ and $r_2$ of PyEA/HEMA was determined. The value of $r_1$ is 0.43, the value of $r_2$ is 2.40 and the value of monomer reactivity ratio $r_1 \times r_2$ is 1.03.

THE EFFECTS OF THE PRESENT INVENTION

The present invention supplies a novel copolymer useful for ocular lens, especially for foldable IOL.

The advantages of copolymers are shown as the following:

1. Exhibit fast recovering property from fold state.
2. Exhibit good refractive index.
3. Good physical strength (tensile strength).
4. Expected property could be obtained through changing composition ratio of each monomer.
5. There would be no trace, even if tweezers are used to operate.
6. Opaque would not occur even if irradiated with laser, and transparency could be maintained.
7. The copolymer could be hydrated after synthesis of the copolymer because there are hydroxyl groups in molecules.
8. The surface of copolymers could easily be treated with a polysaccharide, and the copolymers could be combined with a polysaccharide in a covalent bond state, so it is hardly to be isolated from each other.
9. It is easy to cross link between molecules.
10. The value of monomer reactivity ratio (MRR) $r_1 \times r_2$ of acrylic acid derivative with pyrrolidone group which has the characteristic of monomer component of the copolymers in the present invention, that is to say, components b) and a), accesses 1.0. The value of $r_1 \times r_2$ accessing 1.0 means that the polymerization is ideal.

PREPARATION OF OCULAR LENSES AND EXAMPLES THEREOF

The ocular lenses of the present invention may be formed from the copolymers of the present invention in accordance with known methods, for example, as disclosed in U.S. Pat. No. 5,290,892, U.S. Pat. No. 5,331,073 and U.S. Pat. No. 5,716,403 which are hereby incorporated herein in their entirety including their drawings.

What is claimed is:

1. A copolymer comprising, based on a total weight of 100%, (a) 60 to 80 weight % of a structure unit (I)

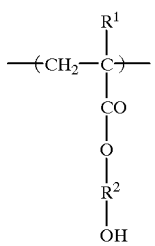

(I)

wherein $R^1$ represents a hydrogen atom or a lower alkyl group, $R^2$ represents an unsubstituted lower alkylene group or a lower alkylene group substituted by a hydroxyl group, said lower alkylene group optionally containing an oxygen atom, (b) 10 to 30 weight % of a structure unit (II)

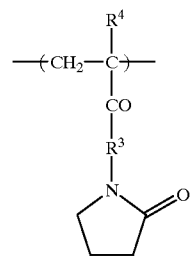

(II)

wherein $R^3$ represents a single bond or

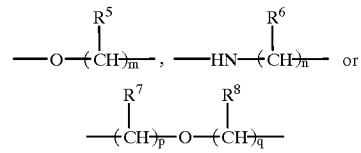

in which $R^5$, $R^6$, $R^7$ and $R^8$ each independently represent a hydrogen atom or a lower alkyl group, m, n, p and q are integers from 1 to 4, and $R^4$ represents a hydrogen atom or a lower alkyl group, and (c) 5 to 20 weight % of a structure unit (III)

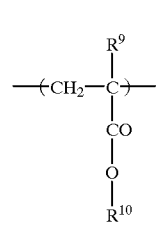

(III)

wherein $R^9$ represents a hydrogen atom or a lower alkyl group and $R^{10}$ represents a lower alkyl group.

2. The copolymer as claimed in claim 1, wherein said copolymer has a molecular weight of ten thousand to one hundred thousand.

3. The copolymer as claimed in claim 1, wherein said $R^1$ represents a hydrogen atom or a methyl group and $R^2$ represents —$(CH_2)_2$— or —$(CH_2)_3$—.

4. The copolymer as claimed in claim 1, wherein said $R^3$ represents —$OCH_2$—, —$OCH_2CH_2$—, —$NHCH_2$— or a single bond and $R^4$ represents a hydrogen atom or a methyl group.

5. The copolymer as claimed in claim 1, wherein said $R^9$ represents a hydrogen atom or a methyl group and $R^{10}$ represents a methyl or an isobutyl group.

6. The copolymer as claimed in claim 1, wherein said $R^1$ represents a hydrogen atom or a methyl group and $R^2$ represents —$(CH_2)_2$— or —$(CH_2)_3$—, $R^3$ represents —$OCH_2$—, —$OCH_2CH_2$, —$NHCH$— or a single bond, $R^4$ represents a hydrogen atom or a methyl group, $R^9$ represents a hydrogen atom or a methyl group and $R^{10}$ represents a methyl or an isobutyl group.

7. The copolymer as claimed in claim 1, wherein said $R^1$ represents a methyl group, $R^2$ represents —$(CH_2)_2$, $R^3$ represents —$OCH_2CH_2$—, $R^4$ represents a methyl group, $R^9$ represents a methyl group and $R^{10}$ represents a methyl group.

8. The copolymer as claimed in claim 1, wherein said structure unit (I) is in an amount of 65 to 75 wt %, said structure unit (II) is in an amount of 15 to 25 wt % and said structure unit (III) is in an amount of 5 to 15 wt %, based on a total weight of 100%.

9. The copolymer as claimed in claim 1, wherein said structure unit (I) is in an amount of 70 wt %, said structure unit (II) is in an amount of 21 wt % and said structure unit (III) is in an amount of 9 wt %.

10. The copolymer as claimed in claim 1, wherein the copolymer comprises 60 to 80 wt % of said structure unit (I), 10 to 30 wt % of said structure unit (II) and 5 to 20 wt % of said structure unit (III), based on a total weight of 100%, wherein $R^1$ represents a hydrogen atom or a methyl group, $R^2$ represents —$(CH_2)_2$—, or —$(CH_2)_3$—, $R^3$ represents —$OCH_2$—, —$OCH_2CH_2$—, —$NHCH_2$— or a single bond, $R^4$ represents a hydrogen atom or a methyl group, $R^9$ represents a hydrogen atom or a methyl group and $R^{10}$ represents a methyl or an isobutyl group.

11. The copolymer as claimed in claim 1, wherein said structure unit (I) is in an amount of 70 wt %, said structure unit (II) is in an amount of 21 wt % and said structure unit (III) is in an amount of 9 wt % and $R^1$ represents a methyl group, $R^2$ represents an ethylene group, $R^3$ represents —$OCH_2CH_2$—, $R^4$ represents a methyl group, $R^9$ represents a methyl group and $R^{10}$ represents a methyl group.

12. The copolymer as claimed in claim 1, in combination with an UV absorber.

13. The copolymer as claimed in claim 12, wherein the UV absorber is in a chemical combination with the copolymer.

14. The copolymer as claimed in claim 13, wherein said UV absorber is in an amount of 0.5–2.0 wt % of the copolymer.

15. The copolymer as claimed in claim 13, wherein said UV absorber is in an amount of 0.8–1.5 wt % of the copolymer.

16. The copolymer as claimed in claim 12, wherein said UV absorber is hydroxyl benzophenone.

17. The copolymer as claimed in claim 12, wherein said UV absorber is an acrylic acid series compound with a hydroxylbenzophenone or a benzotriazole residual group.

18. The copolymer as claimed in claim 1 or 12, wherein the copolymer is cross-linked with a cross-linking agent selected from the group consisting of an acrylate series compound and an acrylamide series compound.

19. The copolymer as claimed in claim 18, wherein said cross-linking agent is selected from the group consisting of ethylene glycol bismethacrylate, diethylene glycol bismethacrylate and N,N'-methylene bisacrylamide and the cross-linking agent is in an amount of 0.01–2.0 wt % of the copolymer.

20. The copolymer as claimed in claim 18, wherein said cross-linking agent is in an amount of 0.1–1.5 wt % of the copolymer.

21. The copolymer as claimed in claim 18, wherein said cross-linking agent is in an amount of 0.5–1.0 wt % of the copolymer.

22. The copolymer as claimed in any of claims 1, 2, wherein a polysaccharide is used to treat a surface of the copolymer.

23. The copolymer as claimed in claim 22, wherein said surface treating is achieved by a covalent bond between the copolymer and polysaccharide.

24. The copolymer as claimed in claim 22, wherein said covalent bond is formed by using divinyl sulfone.

25. The copolymer as claimed in claim 22, wherein said polysaccharide is heparin, hyaluronic acid or a salt thereof.

26. An ocular lens which is formed from the copolymer as claimed in claim 1.

27. A foldable ocular lens which is formed from the copolymer as claimed in claim 1.

28. A foldable ocular lens which is formed from the copolymer as claimed in claim 1 and has the following characteristics:
   a) a refractive index of 1.4–1.6;
   b) a recovering speed from a fold state to an original state being 3–6 seconds;
   c) after being swollen-wetted, a tensile strength of over 10 psi.

29. A foldable ocular lens which is formed from the copolymer as claimed in claim 1 and an UV absorber, wherein a cross-linking agent is used to cross-link the copolymer, and a polysaccharide is used to treat a surface of the copolymer.

30. The foldable ocular lens as claimed in claim 29, wherein said UV absorber is selected from the group consisting of a benzophenone series compound, a benzotriazole series compound and an acrylic acid series compound, with a hydroxylbenzophenone or a benzotriazole residual group; the cross-linking agent is selected from the group consisting of an acrylate series compound and an acrylamide series compound; and the polysaccharide is selected from the croup consisting of heparin, hyaluronic acid and a salt of hyaluronic acid.

31. A copolymer which is copolymerized from the following structural units a), b) and c):

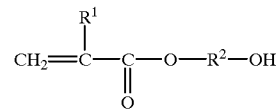

a)

wherein $R^1$ represents a hydrogen atom or a lower alkyl group, $R^2$ represents an unsubstituted lower alkylene group, or a lower alkylene group which is substituted by a hydroxyl group, the lower alkylene group optionally containing an oxygen atom,

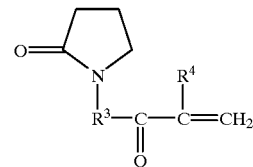

b)

wherein $R^3$ represents a single bond or,

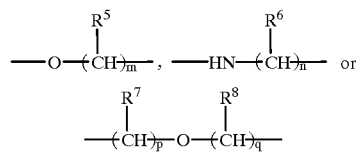

in which $R^5$, $R^6$, $R^7$ and $R^8$ each independently represent a hydrogen atom or a lower alkyl group and m, n, p and q are integers from 1 to 4, and $R^4$ represents a hydrogen atom or a lower alkyl group, c)

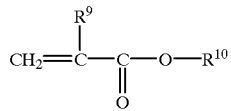

wherein $R^9$ represents a hydrogen atom or a lower alkyl group and $R^{10}$ represents a lower alkyl group.

32. The copolymer as claimed in claim 31, wherein the copolymer has a molecular weight of ten thousand to one hundred thousand.

33. A process for preparing a copolymer as claimed in claim 31, comprising polymerizing said structural units a), b) and c) with a polymerization initiating agent selected from the group consisting of potassium persulfate, ammonium persulfate, benzophenone and methacryloyloxy hydroxylbenzophenone.

34. The copolymer as claimed in claim 18 wherein a polysaccharide is used to treat a surface of the copolymer.

* * * * *